United States Patent [19]

Costantini et al.

[11] Patent Number: 4,612,401

[45] Date of Patent: * Sep. 16, 1986

[54] PROCESS FOR THE PREPARATION OF 4-HYDROXY-2,4,6-TRIMETHYL-2,5-CYCLOHEXADIENONE

[75] Inventors: Michel Costantini, Lyons; Francoise Igersheim, Villeurbanne; Leon Krumenacker, Serezin du Rhone, all of France

[73] Assignee: Rhone-Poulenc Sante, Courbevoie, France

[*] Notice: The portion of the term of this patent subsequent to Dec. 24, 2002 has been disclaimed.

[21] Appl. No.: 713,692

[22] Filed: Mar. 19, 1985

[30] Foreign Application Priority Data

Mar. 22, 1984 [FR] France ............................ 84 04442

[51] Int. Cl.$^4$ ............................................. C07C 45/42
[52] U.S. Cl. ...................................... 568/362; 568/779
[58] Field of Search .............. 568/362, 779, 348, 393

[56] References Cited

U.S. PATENT DOCUMENTS

| | | |
|---|---|---|
| 3,895,069 | 7/1975 | Atkinson et al. ................ 568/362 |
| 3,928,453 | 12/1975 | Atkinson ........................... 568/362 |
| 3,932,475 | 1/1976 | Miyazaki et al. ................. 568/779 |
| 4,284,830 | 8/1981 | Knudsen et al. .................. 568/779 |
| 4,477,682 | 10/1984 | Tomita et al. ..................... 568/362 |
| 4,489,210 | 12/1984 | Judat et al. ........................ 568/348 |

FOREIGN PATENT DOCUMENTS 18606 2/1976 European Pat. Off. ............ 568/362

OTHER PUBLICATIONS

Lamartine et al, J. Org. Chem., vol. 39, pp. 1744-1747 (1974).

Acga Chmica Scandinavica (1982) B36, pp. 675-683, K-E Bergquist et al.; "Electrophilic Chlorination of 4 Methylphenals with Molecular Chlorine, Synthesis of Dimethoxy Aromatics by Methanalysis of 4-Chloro-4-Methylcyclohexa-2,5-Dienones," pp. 675, 678, 682.

Patents Abstracts of Japan, vol. 7, No. 219 (c.188) (1364), Sep. 29, 1983 & JP-A-58-116.435 (Mitsubishi Yas Kagaku K.K.) resume.

Primary Examiner—James H. Reamer
Attorney, Agent, or Firm—Stevens, Davis, Miller & Mosher

[57] ABSTRACT

4-Hydroxy-2,4,6-trimethyl-2,5-cyclohexadienone is made by chlorinating 2,4,6-trimethylphenol with chlorine in an organic solvent in the absence of base while the hydrogen chloride formed is removed as it is formed by physical means and hydrolyzing the reaction mixture with water optionally in the presence of an inorganic base.

5 Claims, No Drawings

PROCESS FOR THE PREPARATION OF 4-HYDROXY-2,4,6-TRIMETHYL-2,5-CYCLOHEXADIENONE

The present invention relates to the preparation of 4-hydroxy-2,4,6-trimethyl-2,5-cyclohexadienone which is an intermediate for the synthesis of trimethylhydroquinone (TMHQ) which is itself a precursor of vitamin E.

It is known to prepare 4-hydroxy-2,4,6-trimethyl-2,5-cyclohexadienone by oxidation of 2,4,6-trimethylphenol, for example with a peracid or molecular oxygen in a basic medium. However, technical implementation of oxidation with air under a pressure in the region of 100 bars presents difficulties and in particular considerable safety problems.

According to the process described by A. Nilson et al, Tetrahedron Letters, 1107 (1975), a 4-hydroxy-2,5-cyclohexadienone can be obtained by solvolysis of a 4-chloro-2,5-cyclohexadienone in the presence of water and a silver salt. 4-Chloro-2,5-cyclohexadienone can be obtained by the action of a chlorinating agent such as gaseous chlorine in an organic solvent such as dichloromethane or dimethylformamide according to K. E. Bergquist et al, Acta Chimica Scandinavica, B 36, 675 (1982) or by the action of chlorine in acetic anhydride according to A. Fischer and G. N. Henderson, Can. J. Chem., 57, 552 (1959) on a 4-alkylphenol.

However, the action of chlorine on 2,4,6-trimethylphenol either produces a mixture of 4-chloro-2,4,6-trimethyl-2,5-cyclohexadienone and 3-chloro-2,4,6-trimethylphenol, or requires the use of a costly solvent such as acetic anhydride in order to obtain good yields. Furthermore, the known conversion of 4-chloro-2,4,6-trimethyl-2,5-cyclohexadienone into the corresponding 4-hydroxy compound requires the use of a silver salt, which makes the process difficult to employ industrially.

To improve the preparation of 4-hydroxy-2,4,6-trimethylcyclohexadien-2,5-one, it is possible to react 2,4,6-trimethylphenol with a halogenating agent in an organic solvent which is inert towards halogenation, in the presence of a base which may be an inorganic base (sodium hydroxide, potassium hydroxide, lithium hydroxide, sodium or potassium carbonate or bicarbonate, lime, calcium carbonate, sodium or potassium acetate) or an organic base (triethylamine, pyridine, a substituted pyridine, dimethylformamide, acetic anhydride) and then to carry out the hydrolysis by stirring in water, optionally in the presence of a base.

It has now been found, and this is the subject of the present invention, that the process for the preparation of 4-hydroxy-2,4,6-trimethyl-2,5-cyclohexadienone can be further improved by carrying out the chlorination of 2,4,6-trimethylphenol in a suitable organic solvent, in the absence of a base, and by removing the hydrogen chloride as it is formed, by physical means, for example by entrainment with a stream of inert gas or by distillation of the solvent, and then hydrolysing the reaction mixture e.g. by stirring with water optionally containing an inorganic base.

Suitable organic solvents are polychlorinated aliphatic hydrocarbons such as methylene chloride or carbon tetrachloride, saturated aliphatic or cycloaliphatic hydrocarbons such as alkanes or cycloalkanes such as pentane, hexane or cyclohexane, aromatic hydrocarbons such as benzene and toluene, chlorinated aromatic hydrocarbons such as chlorobenzenes, ethers such as diethyl ether, diisopropyl ether, methyl tert-butyl ether, tetrahydrofuran or dioxane, esters such as ethyl acetate, and nitriles such as acetonitrile.

The concentration of 2,4,6-trimethylphenol in the solvent may vary within wide limits. It is generally from 0.1 mole/liter to saturation.

In general, a molar ratio chlorinating agent/2,4,6-trimethylphenol of from 0.5:1 to 2:1, preferably from 0.8:1 to 1.2:1, is employed.

The chlorination may be carried out by operating with or without a constant volume of reaction mixture. In constant-volume operation, the volume of the solvent entrained by the gas stream or by distillation is compensated by continuous addition of the same volume of fresh solvent to the reactor.

The chlorination is generally carried out at a temperature of between $-20$ and $+100°$ C. It is advantageous to operate at the boiling point of the solvent, and the temperature may be controlled by controlling the pressure inside the reactor.

The hydrolysis is generally carried out by adding water to the reaction mixture so that the ratio solvent/water is from 0.1:1 to 10:1 and preferably from 0.5:1 to 2:1.

The hydrolysis is generally carried out at a temperature of between $-10°$ C. and the boiling point of the reaction mixture, and preferably between 20° and 60° C.

The hydrolysis may be carried out in the presence or in the absence of an inorganic base such as sodium bicarbonate. When the hydrolysis is carried out in the presence of an inorganic base, the quantity of base employed may be in the molar ratio of 0.1:1 to 2:1 relative to 2,4,6-trimethylphenol employed, and preferably from 0.5:1 to 1.5:1.

4-Hydroxy-2,4,6-trimethyl-2,5-cyclohexadienone can be isolated by the usual extraction methods. It may be isolated in particular by extraction of the organic phase containing 4-hydroxy-2,4,6-trimethyl-2,5-cyclohexadienone with water, followed by evaporation of the aqueous phase after separation or extraction of the aqueous solution with an immiscible organic solvent which is evaporated later.

4-Hydroxy-2,4,6-trimethyl-2,5-cyclohexadienone can be converted to trimethylhydroquinone under the conditions described in French Patent FR No. 73/33,374 published under No. 2,200,225, that is to say by heating to a temperature of at least 100° C. in a non-acidic liquid medium such as water or aqueous methanol.

The following Examples show how the invention can be employed in practice.

EXAMPLE 1

In a cylindrical reactor fitted with a central stirrer, an immersed gas entry tube (fitted with a glass sinter at its end), an outlet tube connected to a wash-bottle containing normal aqueous solution of sodium hydroxide, a thermometer, a dropping funnel and a heating control system, are placed:

2,4,6-trimethylphenol: 13.6 g (100 mmol)
methylene chloride: 200 cc.

Stirring takes place at a speed of 1,000 revolutions/minute. The reaction mixture is heated to about 35° C. A mixture of chlorine and nitrogen (chlorine/nitrogen=⅓ by volume) is then passed through at the rate of approximately 20 liters/hour. The quantity of chlorine introduced is measured by weighing and corresponds to 8 g (112.6 mmol). The outflowing gases are washed with the sodium hydroxide solution present in the wash-bottle. The volume of the reaction mixture is kept constant by continuous addition of methylene chloride in a quantity equal to that entrained with the gas stream. The chlorination time is 30 minutes.

The gas outlet tube is then replaced by a vertical condenser and water (200 cc) containing sodium bicarbonate (8.5 g; 102 mmol) is added quickly. Stirring is then continued for 3 hours at 38° C.

After cooling and separation, the aqueous phase is extracted with methylene chloride (3×50 cc). The organic phases are combined.

The following are determined by gas-liquid chromatography:
2,4,6-trimethylphenol: 0.041 g (0.3 mmol)
4-hydroxy-2,4,6-trimethyl-2,5-cyclonexadienone: 12.4 g (21.75 mmol)

The degree of conversion of 2,4,6-trimethylphenol is 99.7%.

The yield of 4-hydroxy-2,4,6-trimethyl-2,5-cyclohexadienone is 82%.

EXAMPLE 2

The procedure is as in Example 1, with 7.1 g of chlorine (100 mmol) being introduced and nitrogen being replaced by argon.

The following results are obtained:
2,4,6-trimethylphenol: 2.40 g (17.7) mmol)
4-hydroxy-2,4,6-trimethyl-2,5 cyclohexadienone: 10.2 g (67.1 mmol)

The degree of conversion of 2,4,6-trimethylphenol is 82.3%.

The yield of 4-hydroxy-2,4,6-trimethyl-2,5-cyclohexadienone is 81.6%.

EXAMPLE 3

The same reactor as that described in Example 1 is employed, in which the outlet tube is connected to a system which permits the solvent to be distilled off in the course of the chlorination.

The following are charged:
2,4,6-trimethylphenol: 13.6 g (100 mmol)
methylene chloride: 200 cc Stirring is carried out at a speed of 1,000 revolutions/minute. The reaction mixture is heated to reflux (40° C.), a stream of gaseous chlorine is then passed through for 40 minutes. The total quantity of chlorine introduced is measured by weighing and corresponds to 7.7 g (108 mmol). At the same time as chlorine is passed through, methylene chloride is distilled off while the reaction volume is kept constant by continuous addition of methylene chloride. The total quantity of methylene chloride distilled is 350 cc.

The procedure is then as in Example 1. The following are determined by gas-liquid chromatography:
2,4,6-trimethylphenol: 1.8 g (13.3 mmol)
4-hydroxy-2,4,6-trimethyl-2,5-cyclohexadienone: 10.6 g (69.6 mmol)

The degree of conversion of 2,4,6-trimethylphenol is 86.7%. The yield of 4-hydroxy-2,4,6-trimethyl-2,5-cyclohexadienone is 80%.

EXAMPLE 4

The procedure is as in Example 1 but 7.1 g of chlorine (100 mmol) are employed and sodium bicarbonate is left out.

The following are determined by gas-liquid chromatography:
2,4,6-trimethylphenol: 2.6 g (19.2 mmol)
4-hydroxy-2,4,6-trimethyl-2,5-cyclohexadienone: 9.8 g (64.4 mmol)

The degree of conversion of 2,4,6-trimethylphenol is 80.8%.

The yield of 4-hydroxy-2,4,6-trimethyl-2,5-cyclohexadienone is 79.7%.

EXAMPLE 5

The procedure is as in Example 3 but the chlorination is carried out over 1 hour 5 minutes and methylene chloride is distilled off (90 cc).

After determination by gas-liquid chromatography, the following results are obtained:
2,4,6-trimethylphenol: 6.6 mmol
4-hydroxy-2,4,6-trimethyl-2,5-cyclohexadienone: 71.0 mmol The degree of conversion of 2,4,6-trimethylphenol is 93.3%. The yield of 4-hydroxy-2,4,6-trimethyl-2,5-cyclohexadienone is 76%.

EXAMPLE 6

The procedure is carried out in the same apparatus as in Example 3. The following are charged:
2,4,6-trimethylphenol: 13.6 g (100 mmol)
methyl tert-butyl ether: 200 cc.

Stirring is carried out at a speed of 1,000 revolutions/minute. The reaction mixture is heated to reflux (38.5° C. at a pressure of 410 mm Hg; 54.3 kPa). A stream of gaseous chlorine is then passed through for 29 minutes. Th total quantity of chlorine introduced is 7.9 g (111 mmol). At the same time as chlorine is passed through, methyl tert-butyl ether is distilled off while the reaction volume is kept constant by continuous addition of methyl butyl ether. The total quantity of methyl tert-butyl distilled off is 470 cc.

The procedure is then as in Example 1.

The following are determined by gas-liquid chromatography:
2,4,6-trimethylphenol: 12.9 mmol
4-hydroxy-2,4,6-trimethyl-2,5-cyclohexadienonel 64.1 mmol.

The degree of conversion of 2,4,6-trimethylphenol is 87.1%.

The yield of 4-hydroxy-2,4,6-trimethyl-2,5-cyclohexadienone is 73.5%.

We claim:

1. Process for the preparation of 4-hydroxy-2,4,6-trimethyl-2,5-cyclohexadienone which comprises reacting 2,4,6-trimethylphenol with chlorine in an inert organic solvent selected from the class consisting of an aliphatic or cycloaliphatic hydrocarbon, a polychlorinated aliphatic hydrocarbon, an aromatic hydrocarbon, a chlorinated aromatic hydrocarbon, an ether, an ester or a nitrile, in the absence of base, removing the hydrogen chloride as it is formed by the passage of a stream of inert gas through the reaction mixture or by distillation of the organic solvent under ambient or reduced pressure, and hydrolysing the reaction mixture with water in the presence or absence of an inorganic base.

2. A process according to claim 1, in which the volume of the reaction mixture is maintained by continuous addition of fresh organic solvent to replace the solvent distilled off.

3. A process according to claim 1, in which the concentration of 2,4,6-trimethylphenol in the organic solvent is from 0.1 mole per litre to saturation.

4. A process according to claim 1, in which the chlorination is carried out at a temperature from −20° to +100° C.

5. A process according to claim 1, in which the molar ratio of chlorine used to 2,4,6-trimethylphenol is from 0.5:1 to 2:1.

* * * * *